US008208986B2

(12) United States Patent
Duerk et al.

(10) Patent No.: US 8,208,986 B2
(45) Date of Patent: Jun. 26, 2012

(54) STEADY STATE DARK BLOOD MAGNETIC RESONANCE IMAGING

(76) Inventors: Jeffrey L. Duerk, Avon Lake, OH (US); Mark A. Griswold, Shaker Heights, OH (US); Jeffrey L. Sunshine, Pepper Pike, OH (US); Jamal J. Derakhshan, Cleveland Heights, OH (US)

(*) Notice: Subject to any disclaimer, the term of this patent is extended or adjusted under 35 U.S.C. 154(b) by 474 days.

(21) Appl. No.: 12/283,196

(22) Filed: Sep. 10, 2008

(65) Prior Publication Data
US 2010/0063380 A1 Mar. 11, 2010

(51) Int. Cl.
*A61B 5/05* (2006.01)
(52) U.S. Cl. ........................ 600/410; 324/309
(58) Field of Classification Search ................ 600/407, 600/410–413, 418, 425, 427; 324/306–307, 324/309, 312, 317, 319; 128/653
See application file for complete search history.

(56) References Cited

U.S. PATENT DOCUMENTS

| 5,541,514 | A * | 7/1996 | Heid et al. ............... 324/309 |
| 6,078,175 | A * | 6/2000 | Foo ........................... 324/306 |
| 6,566,876 | B2  | 5/2003 | Fautz |
| 7,071,689 | B2 * | 7/2006 | Golay et al. ............... 324/309 |
| 7,187,170 | B1 * | 3/2007 | Hargreaves et al. ....... 324/307 |
| 7,253,620 | B1 * | 8/2007 | Derbyshire et al. ........ 324/307 |
| 2004/0204643 | A1 | 10/2004 | Jesmanowicz |
| 2005/0209517 | A1 * | 9/2005 | Diab et al. ................ 600/323 |
| 2006/0058634 | A1 | 3/2006 | Ikezaki |
| 2007/0255129 | A1 * | 11/2007 | Du et al. ................... 600/410 |

OTHER PUBLICATIONS

PCT Intl. Search Report and Written Opinion in co-pending PCT Application No. PCT/US09/56350 (filed Sep. 9, 2009; having a mailing date of Oct. 30, 2009.

* cited by examiner

*Primary Examiner* — Brian Casler
*Assistant Examiner* — Michael N Fisher
(74) *Attorney, Agent, or Firm* — John T. Kalnay (57) ABSTRACT

Systems, methods, and other embodiments associated with steady state dark blood magnetic resonance imaging MRI are described. One example method includes controlling an MRI apparatus to produce a steady state pulse sequence. The example method may also include controlling the MRI apparatus to generate radio frequency (RF) energy and magnetic gradients associated with the steady state pulse sequence. The steady state pulse sequence is different from conventional steady state pulses in that it is characterized by regularly spaced slice selection excitation pulses to excite a region to be imaged in an object to be imaged using a consistent repetition time (TR), a set of readout modules, and a set of a magnetization preparation modules. A magnetization preparation module is characterized by gradients associated with imaging not being active, gradients associated with slice selection being active, and RF pulses associated with slice selection being active.

20 Claims, 10 Drawing Sheets

STEADY STATE DARK BLOOD MAGNETIC RESONANCE IMAGING

COPYRIGHT NOTICE

A portion of the disclosure of this patent document contains material that is subject to copyright protection. The copyright owner has no objection to the facsimile reproduction of the patent document or the patent disclosure as it appears in the Patent and Trademark Office patent file or records, but otherwise reserves all copyright rights whatsoever.

BACKGROUND

In magnetic resonance imaging (MRI), some received signals may be useful for imaging a structure (e.g., blood vessel wall, heart valve). Other received signals may not be useful for imaging that structure. For example, signal from a blood vessel wall may be useful for imaging the blood vessel wall while signal from blood flowing through that blood vessel may not be useful for imaging the blood vessel wall. Indeed, it may be desirable to suppress signal from blood flowing through a blood vessel to facilitate acquiring a clear image of the blood vessel wall. Similarly, it may be desirable to suppress signal from blood flowing through a heart valve to facilitate acquiring a clear magnetic resonance (MR) image of the heart valve.

Several conventional approaches have attempted to image tissue and/or structures in the presence of flowing blood. These may be referred to as "dark blood" imaging techniques. In dark blood imaging, signal is received from the structure of interest. However, signal is not received from blood that is near the structure of interest or signal that is received from the blood has properties that make those signals distinguishable from signals from the structure of interest.

One previous dark blood imaging technique is described in "Dark-Blood True-FISP Imaging Using Dual Steady States", Duerk, et al., Proc. Intl. Soc. Mag. Reson. Med 11 (2004). This technique involved establishing separate steady states in and out of a plane of interest. This technique produced excellent suppression of inflowing spins and consistent TrueFISP contrast within a slice. However, the minimum repetition time (TR) of the sequence was extended by at least 1.5 ms over a standard TrueFISP sequence to permit inclusion of a slab-selection radio frequency (RF) pulse and an extra gradient area. Another previous technique is described in "A Radial Steady State Free Precession Approach", Duerk, et al., Proc. Intl. Soc. Mag. Reson. Med. 11 (2004). This technique involved a radial steady state free precession (SSFP) sequence with random amplitude velocity encoding gradients applied prior to data acquisition. Thus, a standard TrueFISP sequence was modified by adding a random bipolar gradient prior to radial SSFP data acquisition in each TR. This increased the TR. Thus, previous attempts to produce dark blood (DB) contrast in steady state sequences have typically lengthened the repetition time (TR) and/or disturbed the steady state of a slice to be acquired. The longer TR may introduce and/or exacerbate issues associated with eddy current artifacts, increased off-resonance banding artifacts, and so on.

In MRI, different types of contrast can be generated by applying different radio frequency (RF) and magnetic field gradient pulses to a subject area. These different types of contrast can be used to distinguish between items. Additionally, different types of contrast may be available because a subject may be comprised of different materials. For example, a subject area may include tissue and blood. The tissue may include fat and water. Different materials to which different RF and magnetic field gradient pulses are applied may produce different magnetic resonance (MR) signals. Once again, the different MR signals may be used to distinguish between items. Dark blood imaging involves either acquiring a first type of signal from an item (e.g., blood vessel wall) near blood and a second type of signal from the blood near the item or acquiring signal from an item (e.g., heart valve) near blood while preventing the blood near the item from generating a signal. The blood near an item may not be static. For example, blood may be flowing in a blood vessel to be imaged. Similarly, blood may be moving through a valve to be imaged. Either suppressing the signal from the blood or making the item to be imaged and the blood near the item to be imaged have different MR signals facilitate acquiring better MR images of the item to be imaged.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Example systems and methods perform dark blood imaging by producing a modified steady state (e.g., TrueFISP) pulse sequence and acquiring MR signals in response to applying the modified steady state pulse sequence to a subject. A steady state sequence is a field or gradient echo sequence in which a non-zero steady state develops for components of magnetization. For example, a non-zero steady state may develop for both transverse and longitudinal magnetization. A steady state sequence is also a sequence in which the TR is shorter than the T1 and T2 times of tissue being imaged. In a steady state sequence, if the RF pulses are close enough together, the MR signal will never completely decay and thus spins in the transverse plane may never completely dephase. Thus, magnetization preparation modules (e.g., saturation, inversion, tagging) may be incorporated into linear preparation schemes employed in steady state sequences, including TrueFISP sequences. Since readout modules may be replaced with preparation modules, TR is not increased. This distinguishes example techniques from conventional techniques that perform additional preparation and/or saturation work and thus increase TR.

TrueFISP is true, fast imaging with steady state precession. TrueFISP is a coherent technique that uses a fully balanced gradient waveform. Thus, in a TrueFISP sequence the gradient areas sum to zero in each TR. See, for example, gradient areas illustrated in the top half (symmetric) of FIG. 8. In TrueFISP, image contrast depends on flip angle, $T2/T2^*/T1$, TR, and resonance offset angle. Recall that T1 refers to longitudinal or spin-lattice relaxation, that T2 refers to transverse of spin-spin relaxation, and TR refers to repetition time. TrueFISP has conventionally been employed for cardiac MRI due to short imaging times and acceptable contrast between blood and structures including, for example, the myocardium. Example systems and methods improve on a conventional TrueFISP sequence and on other conventional steady state sequences for dark blood imaging by replacing a readout module in the sequence with a different type of module, a magnetization preparation. Since the magnetization preparation module (e.g., saturation, tagging, inversion) replaces a readout module, TR is not increased.

In one example, a steady state pulse sequence readout module is replaced with a saturation module. During the saturation module, the gradients and RF pulses for slice selection of the imaging slice are still played out to facilitate keeping a slice to be imaged in steady state. However, the gradients associated with imaging are eliminated and replaced with RF pulses and gradients that produce slab saturation outside the imagine slice. These gradients may be non-symmetric about the center of TR. However, the first moment of a gradient axis over TR is zero to maintain steady state free precession. An example non-symmetric gradient is illustrated in the bottom half (non-symmetric) of FIG. 8.

Figure 1:
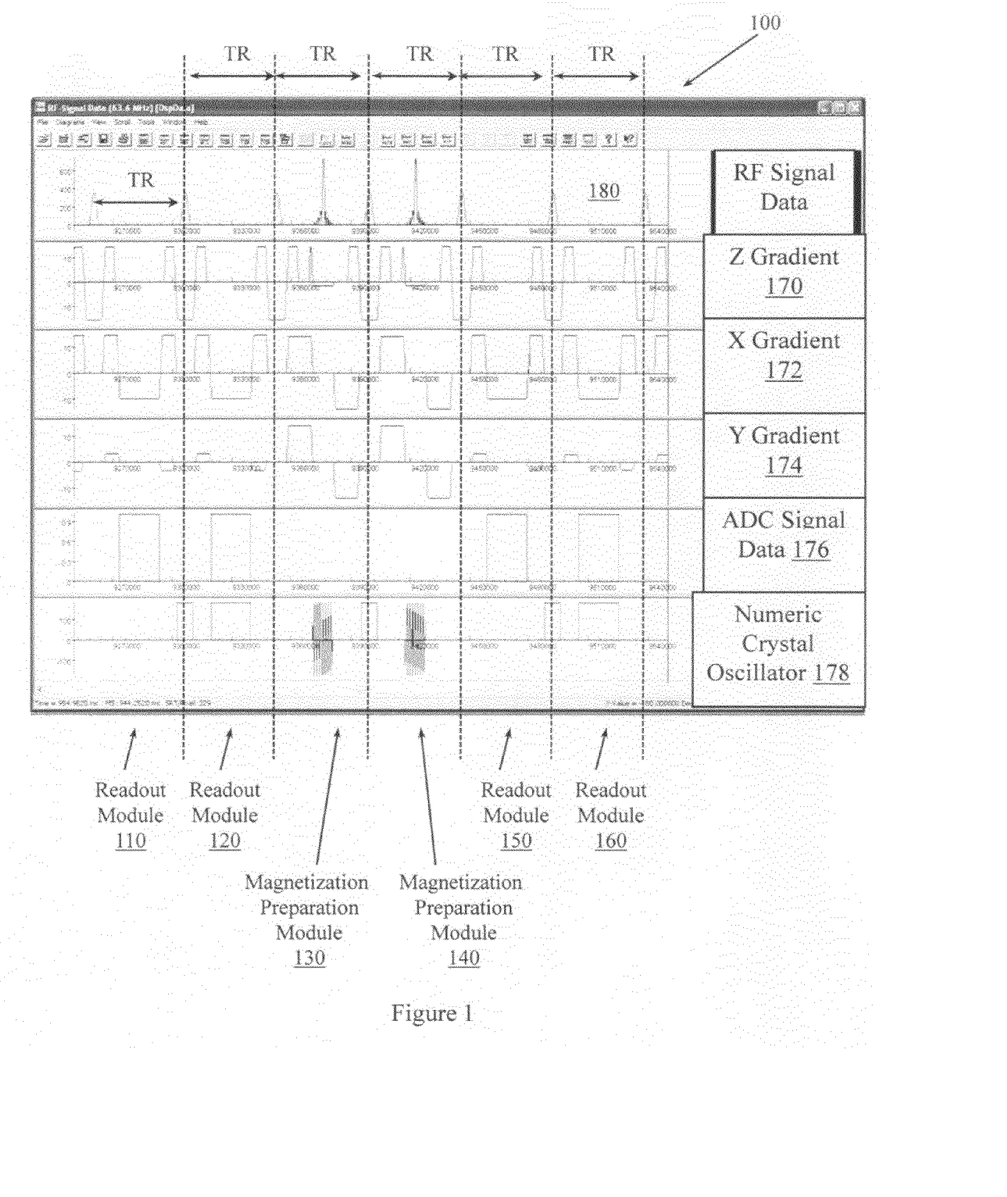
FIG. 1 illustrates an example steady state pulse sequence associated with steady state dark blood MRI.

In one example, saturation modules may be paired to facilitate minimizing, for example, eddy current artifacts. In other examples, a readout module may be replaced with an inversion module, with a partial inversion module, with a tagging module, and so on. Recall that a readout module may include a phase encoding and readout gradient. A saturation module may include RF pulses that excite and, in conjunction with gradients, dephase magnetization in regions (e.g., slabs) near an imaging slice. Thus, in a saturation module, a gradient is on at the same time as RF is on. This is illustrated in FIG. 1, which is a pulse sequence diagram of an example modified TrueFISP pulse sequence. FIG. 1 is described in greater detail below. One skilled in the art will appreciate that non-linear phase RF pulses may be employed to maximize dephasing for saturation slab excitation. In this example, the slice select gradient may be symmetric about the center of TR.

Figure 10:
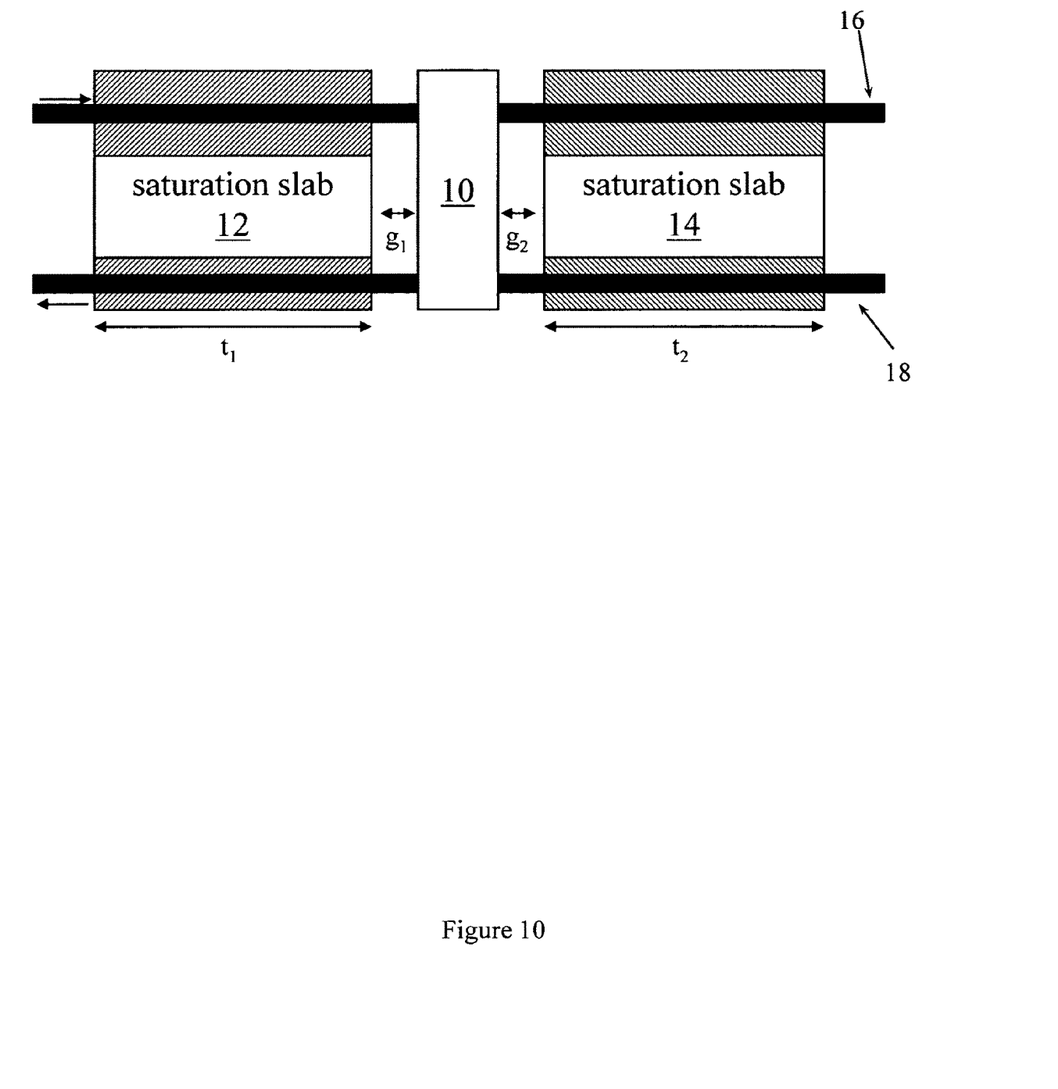
FIG. 10 illustrates an imaging slice and related saturation slabs.

MR images are typically acquired in a series of slices. A portion of a region of interest (e.g., blood vessel wall, valve) may be what a viewer wants to image in a slice. However blood may flow into the slice being imaged from slices adjacent to the slice being imaged. For example, in an axial slice, blood may flow into the slice being imaged from slices both above and below the slice being imaged. FIG. 10 illustrates this concept. FIG. 10 depicts a relation of two saturation slabs to an imaging slice(s). It may be desired to image slice 10. However, blood may flow into slice 10 from saturation slab 12 and/or saturation slab 14. If untreated, spins arriving from saturation slabs 12 and/or 14 may compromise the quality of an image of slice 10. Thus, one or both of saturation slabs 12 and 14 can be applied to suppress signal from blood flow coming from above and/or below the slice to be imaged. In one example, the thickness (e.g., t1, t2) of the saturation slabs 12 and/or 14 and the gaps (e.g., g1, g2) from the saturation slabs 12 and 14 to the imaging slice 10 can be freely controlled. Rectangles 16 and 18 represent hypothetical blood vessels with blood flow coming from above and below the imaging slice 10. Due to the saturation modules applied in the modified steady state pulse sequence, the blood signal is attenuated as it flows through the imaging slice 10. While slices and slabs are described, more generally saturation may occur in a saturation region. Similarly, "magnetization preparation" and imaging may occur in regions.

Consider an axial slice. Example systems and methods facilitate performing dark blood preparations in regions outside an imaging slice to suppress signals from blood entering the imaging slice from above and/or below. Example systems and methods may also facilitate performing dark blood preparations in preparation regions (e.g., slices, slabs) having other orientations, where the orientation may depend, at least in part, on the orientation (e.g., coronal, longitudinal, axial) of the slice being imaged. In one example, dark blood preparations may be performed using saturation modules that replace readout modules in an improved steady state (e.g., TrueFISP) sequence. In different examples, different parameters associated with a saturation slice can be configured. Configurable parameters may include, for example, the position of a saturation slice relative to an imaging slice, the thickness of the saturation slice, and so on. The frequency of magnetization preparation may vary during an acquisition depending on the location being encoded in k-space. The ratio of readout modules to saturation modules may also be configurable.

While TrueFISP has been described above, one skilled in the art will appreciate that readout modules in other steady state sequences may also be replaced with other magnetization preparation modules (e.g., saturation, inversion, tagging) to improve imaging. These steady state sequences include, for example, FLASH (Fast Low Angle Shot), FISP (fast imaging steady state precession), PSIF (a gradient reversed form of FISP), and so on.

While a blood vessel wall and a heart valve have been described, one skilled in the art will appreciate that example systems and methods may have other applications. For example, a steady state imaging pulse sequence using a readout module substituted with a magnetization preparation module may be employed in cardiac imaging, vessel wall imaging, vascular intervention, vascular imaging, and other applications where there is fluid motion in a region to be imaged. Cardiac imaging may include imaging, for example, for wall motion abnormalities, for fatty infiltration, for valve defects, and so on. Vessel wall imaging may include imaging, for example, for atherosclerosis, for vasculitis, for dissection, and so on. Vascular intervention imaging may include imaging, for example, for catheter guidance, for pulmonary vein ablations, for stem cell delivery, and so on. Vascular imaging may include imaging, for example, for peripheral artery disease, for indicia of stroke, for arteriovenous malformations, and so on. Imaging for fluid motion may include imaging, for example, for cerebrospinal fluid motion, for urine motion, for hydraulic fluid motion, and so on. One skilled in the art will appreciate that the imaging may include both conventional "in the bore" MRI with surface coils and high resolution catheter based imaging.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

ASIC: application specific integrated circuit.
CD: compact disk.
CD-R: CD recordable.
CD-RW: CD rewriteable.
DVD: digital versatile disk and/or digital video disk.
HTTP: hypertext transfer protocol.
LAN: local area network.
PCI: peripheral component interconnect.
PCIE: PCI express.
RAM: random access memory.
DRAM: dynamic RAM.
SRAM: synchronous RAM.
ROM: read only memory.
EEPROM: electrically erasable PROM.
USB: universal serial bus.
WAN: wide area network.

"Computer component", as used herein, refers to a computer-related entity (e.g., hardware, firmware, software in execution, combinations thereof). Computer components may include, for example, a process running on a processor, a processor, an object, an executable, a thread of execution, and a computer. A computer component(s) may reside within a process and/or thread. A computer component may be localized on one computer and/or may be distributed between multiple computers.

"Computer communication", as used herein, refers to a communication between computing devices (e.g., computer, personal digital assistant, cellular telephone) and can be, for example, a network transfer, a file transfer, an applet transfer, an email, an HTTP transfer, and so on. A computer communication can occur across, for example, a wireless system (e.g., IEEE 802.11), an Ethernet system (e.g., IEEE 802.3), a token ring system (e.g., IEEE 802.5), a LAN, a WAN, a point-to-point system, a circuit switching system, a packet switching system, and so on.

"Computer-readable medium", as used herein, refers to a medium that stores signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

In some examples, "database" is used to refer to a table. In other examples, "database" may be used to refer to a set of tables. In still other examples, "database" may refer to a set of data stores and methods for accessing and/or manipulating those data stores.

"Data store", as used herein, refers to a physical and/or logical entity that can store data. A data store may be, for example, a database, a table, a file, a data structure (e.g. a list, a queue, a heap, a tree) a memory, a register, and so on. In different examples, a data store may reside in one logical and/or physical entity and/or may be distributed between two or more logical and/or physical entities.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Software", as used herein, includes but is not limited to, one or more executable instruction that cause a computer, processor, or other electronic device to perform functions, actions and/or behave in a desired manner. "Software" does not refer to stored instructions being claimed as stored instructions per se (e.g., a program listing). The instructions may be embodied in various forms including routines, algorithms, modules, methods, threads, and/or programs including separate applications or code from dynamically linked libraries.

"User", as used herein, includes but is not limited to one or more persons, software, logics, computers or other devices, or combinations of these.

FIG. 1 illustrates a display 100 of RF pulses, gradients, analog to digital converter signals, and numerically controlled oscillator signals associated with an example TrueFISP pulse sequence associated with steady state dark blood MRI. Display 100 can be divided vertically into columns corresponding to a readout module 110, a readout module 120, a magnetization preparation module 130, a magnetization preparation module 140, a readout module 150, and a readout module 160. Display 100 can also be divided horizontally into an RF signal data portion 180, a z-gradient portion 170, an x-gradient portion 172, a y-gradient portion 174, an ADC signal data portion 176, and a numerical crystal oscillator portion 178.

One skilled in the art will understand the difference between the steady state pulse sequence illustrated in display 100 and previous pulse sequences. The pulse sequence includes readout modules 110, 120, 150, and 160 and magnetization preparation modules 130 and 140. One skilled in the art will distinguish the presence of modified gradients and additional RF pulses during magnetization preparation modules 130 and 140 along with the absence of gradients associated with imaging. Thus, one skilled in the art will appreciate that the magnetization preparation modules 130 and 140 may be used, for example, to saturate spins in a slice outside a slice to be imaged during readout modules 150 and 160. One skilled in the art will readily contrast the regularly spaced TRs in the pulse sequence in display 100 from the irregularly spaced TRs and inconsistent TRs associated with other methods. This contrast is made clear in FIG. 9.

Figure 9:
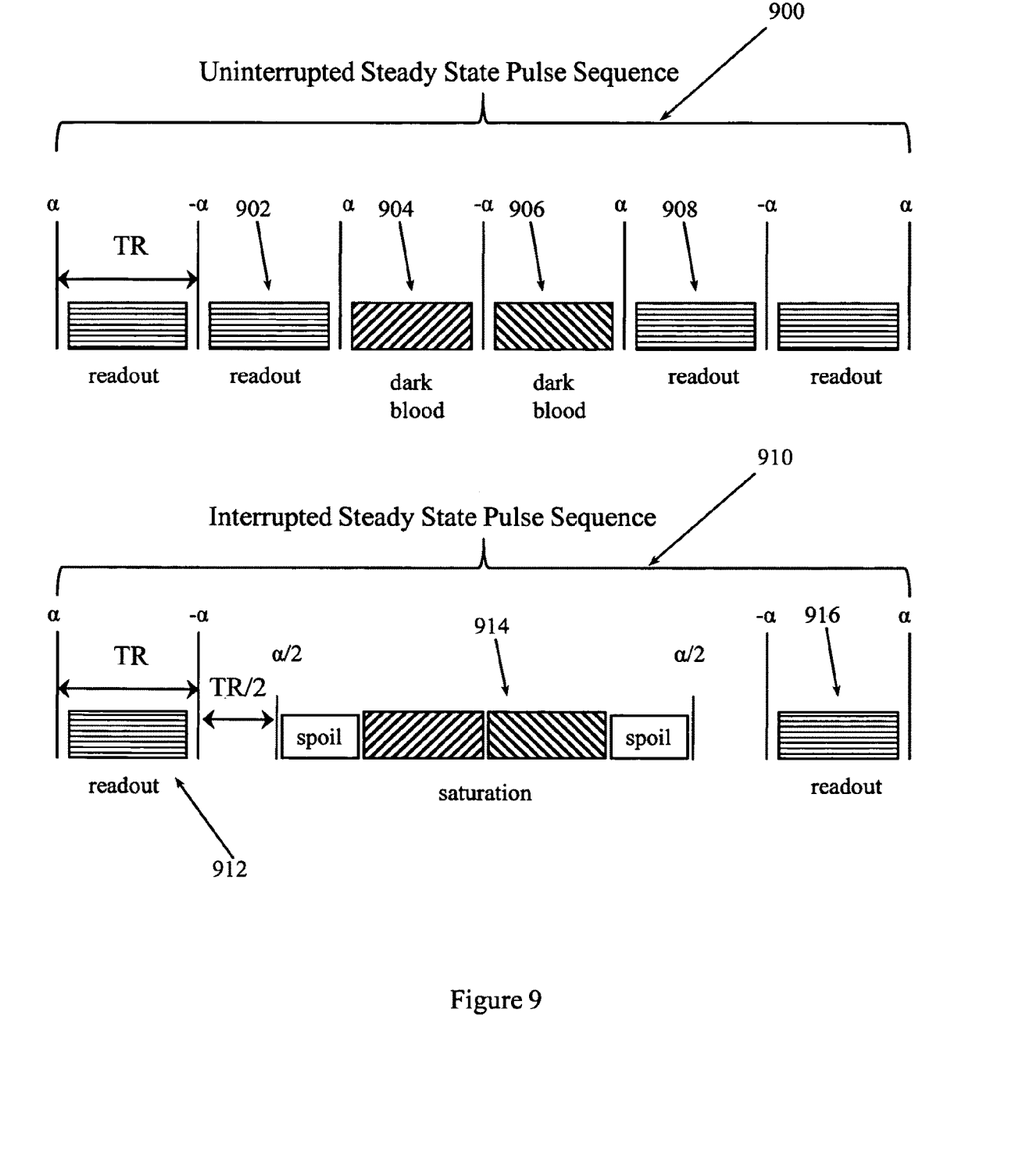
FIG. 9 illustrates both an uninterrupted steady state pulse sequence associated with saturation of blood and an interrupted steady state pulse sequence associated with saturation of fat.

FIG. 9 illustrates an uninterrupted steady state pulse sequence 900 and an interrupted steady state pulse sequence 910. The uninterrupted sequence 900 includes readout modules 902 and 908 along with dark blood modules 904 and 906. The dark blood modules may be, for example, saturation modules. Note the regularly spaced TRs and the consistently sized TRs. Compare this to interrupted sequence 910, which includes readout modules 912 and 916 and a saturation module 914. Sequence 910 clearly does not include regularly spaced TRs and does not include consistently sized TRs.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is to be appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. For purposes of simplicity of explanation, the illustrated methodologies are shown and described as a series of blocks. However, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 2:
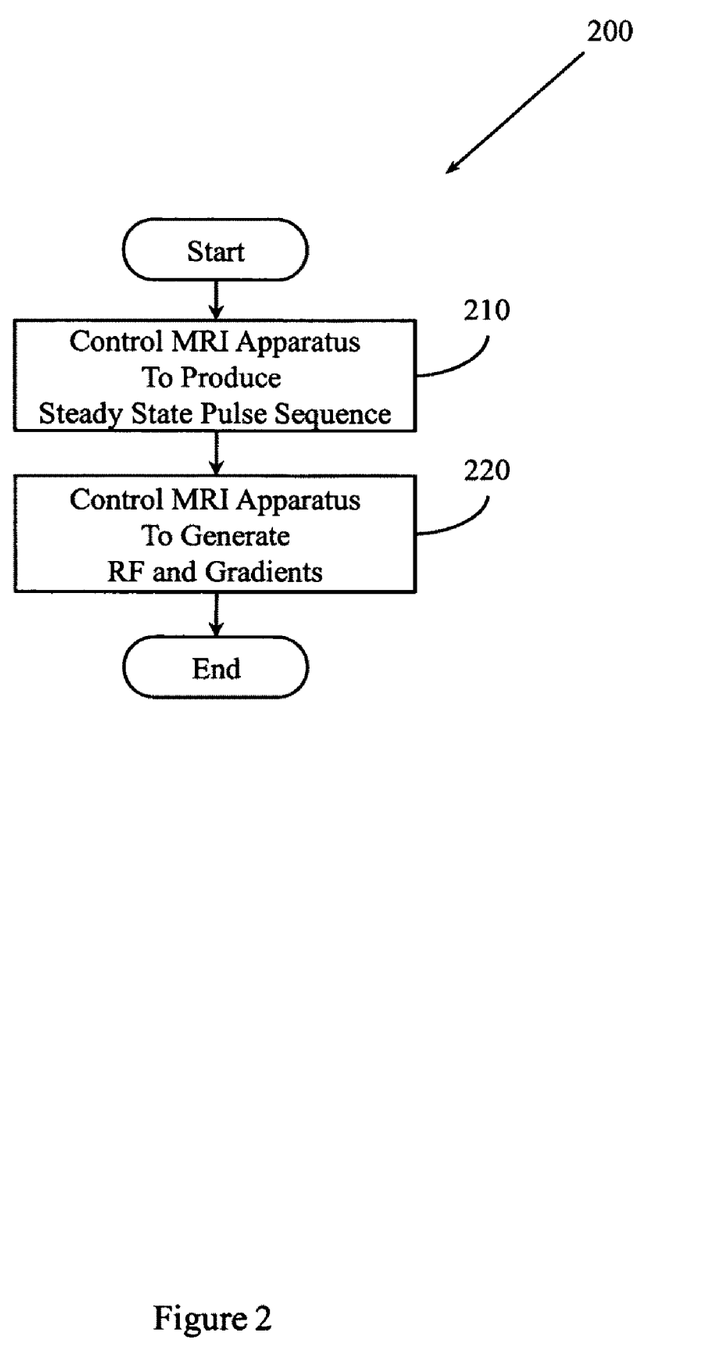
FIG. 2 illustrates an example method associated with steady state dark blood magnetic resonance imaging (MRI).

FIG. 2 illustrates an example method 200 associated with steady state dark blood MRI. Method 200 may include, at 210, controlling an MRI apparatus to produce a steady state pulse sequence. The steady state pulse sequence is different from conventional pulse sequences. The steady state pulse sequence is characterized by at least three attributes. First, the steady state pulse sequence includes regularly spaced slice selection excitation pulses to excite a region to be imaged in the object to be imaged using a consistent repetition time (TR). Second the steady state pulse sequence includes a readout module. Third, the steady state pulse sequence includes a magnetization preparation module. The inclusion of this magnetization preparation module without increasing TR that provides one distinction over conventional sequences. During a magnetization preparation module a gradient associated with imaging is not active, a gradient associated with slice selection is active, and RF pulses associated with slice selection are active.

In one example, the magnetization preparation module is a saturation module. During the saturation module the method 200 includes, at 210, producing a pulse sequence that is to control production of a gradient associated with slice selection and RF pulses associated with slice selection to excite a set of saturation regions located outside the region to be imaged. These regions may be slabs, slices, and so on, where spins that may flow into a region to be imaged are located. Since flow rates may vary, the location, size, and/or orientation of the regions may be configurable. The TrueFISP pulse sequence may be paired to avoid eddy currents. Thus, in one example the steady state pulse sequence may include a repeating pattern of an even number of consecutive readout modules followed by an even number of magnetization preparation sequences. In a non-pairing example, gradient pre-compensation or gradient design may mitigate eddy currents.

In one example, method 200 includes, at 210, causing the frequency of the saturation modules to change during acquisition to vary the amount of saturation in relation to the region in k-space being encoded during the surrounding readout modules. For example, the composition of the pulse sequences may be changed to apply a relatively larger number of saturation modules near the contrast determining center of k-space and to apply a relatively smaller number of saturation modules near the resolution determining outer region of k-space. While a saturation module has been described, it is to be appreciated that a tip angle associated with the magnetization preparation module need not be 90 degrees. In some examples, a non 90 degree tip angle may be employed to cause magnetization to traverse a null point during subsequent readout modules.

While a saturation module has been described, it is to be appreciated that there may be different types of magnetization preparation modules. For example, the magnetization preparation module may be an inversion module, a tagging module, and so on. Thus, in one example, method 200 may include producing, at 210, a pulse sequence that will, at 220, control an MR gradient, and RF pulses to produce two different excitations in two different sets of spins during the tagging module. The first excitation may be produced in spins associated with an item that is moving in an imaging region. A second excitation may be produced in spins that are associated with an item that is substantially static in the imaging region.

Method 200 may also include, at 220, controlling the MRI apparatus to generate radio frequency (RF) energy and magnetic gradients associated with the steady state pulse sequence produced at 210. Signals from which an MR image of the object to be imaged can be reconstructed are to be acquired during a readout module. The signals from which an MR image can be reconstructed are generated in response to the MRI apparatus generating the RF pulses and gradients at 220. The RF energy and magnetic gradients may comport with different steady state pulse sequences. In different embodiments the steady state pulse sequence may be, for example, a TrueFISP sequence, a FLASH sequence, a FISP sequence, a PSIF sequence, and so on.

Figure 8:
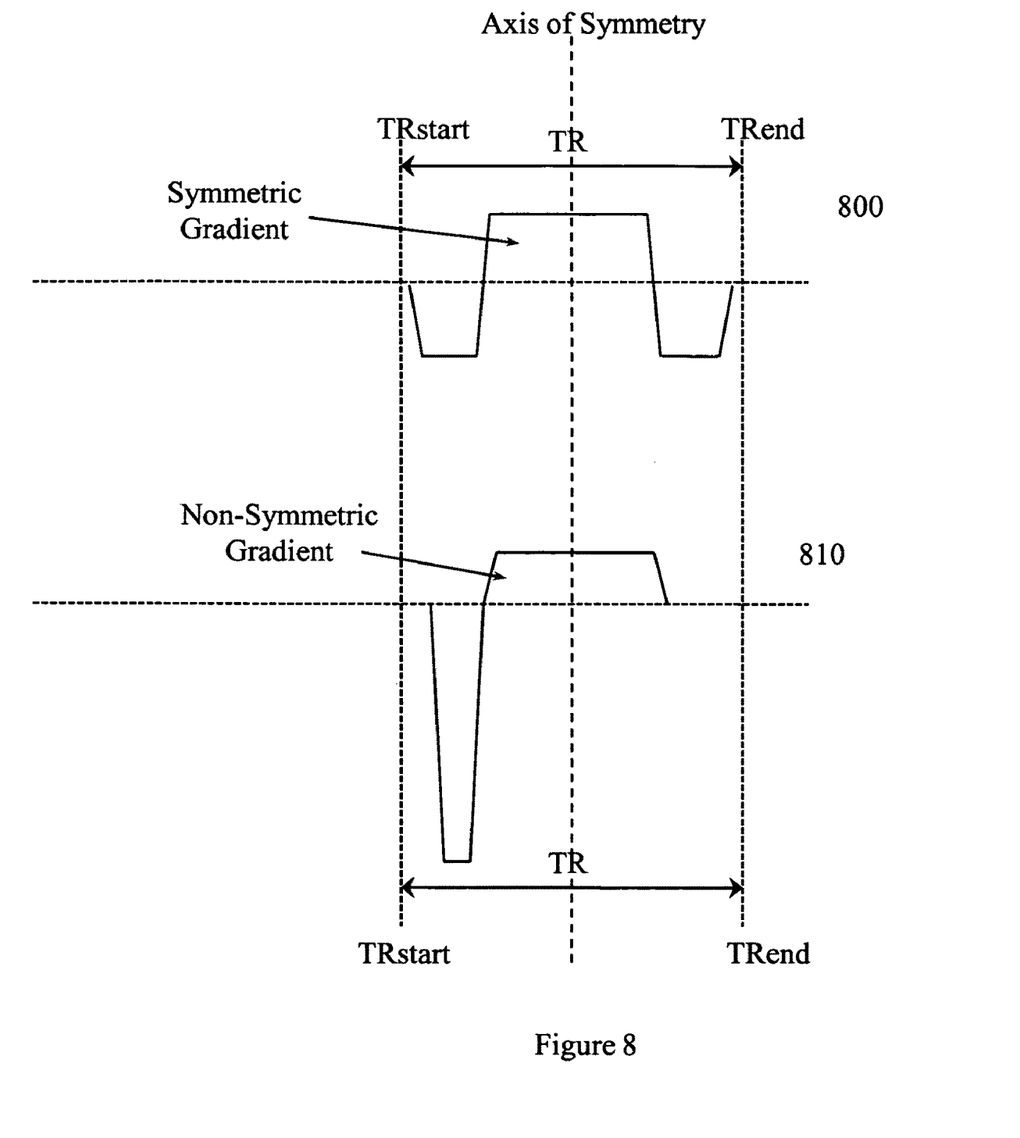
FIG. 8 illustrates a symmetric gradient associated with image acquisition and an asymmetric gradient associated with saturation.

Controlling the MRI apparatus at 220 may include controlling gradients during a magnetization preparation module. The gradients may be controlled to be non-symmetric gradients as illustrated in both FIG. 1 and FIG. 8. FIG. 8 illustrates a symmetric gradient 800 and a non-symmetric gradient 810. Symmetric gradient 800 may be produced during a readout module. Anti-symmetric gradient 820 may be produced during a magnetization preparation (e.g., saturation) module. One skilled in the art will appreciate that a readout module may include phase encoding gradients that are anti-symmetric as well as readout and slice select gradients that are symmetric. One skilled in the art will also appreciate that a magnetization preparation module may also include both symmetric and non-symmetric gradients.

While FIG. 2 illustrates various actions occurring in serial, it is to be appreciated that various actions illustrated in FIG. 2 could occur substantially in parallel. By way of illustration, a first process could produce a pulse sequence and a second process could control an MRI apparatus based, at least in part, on the pulse sequence. Since the pulse sequence may vary as described above, the first process may be filling a pulse sequence data store while the second process is emptying that pulse sequence data store. While two processes are described, it is to be appreciated that a greater and/or lesser number of processes could be employed and that lightweight processes, regular processes, threads, and other approaches could be employed.

In one example, a method may be implemented as computer executable instructions. Thus, in one example, a computer-readable medium may store computer executable instructions that if executed by a machine (e.g., processor) cause the machine to perform the methods described and claimed herein.

Figure 3:
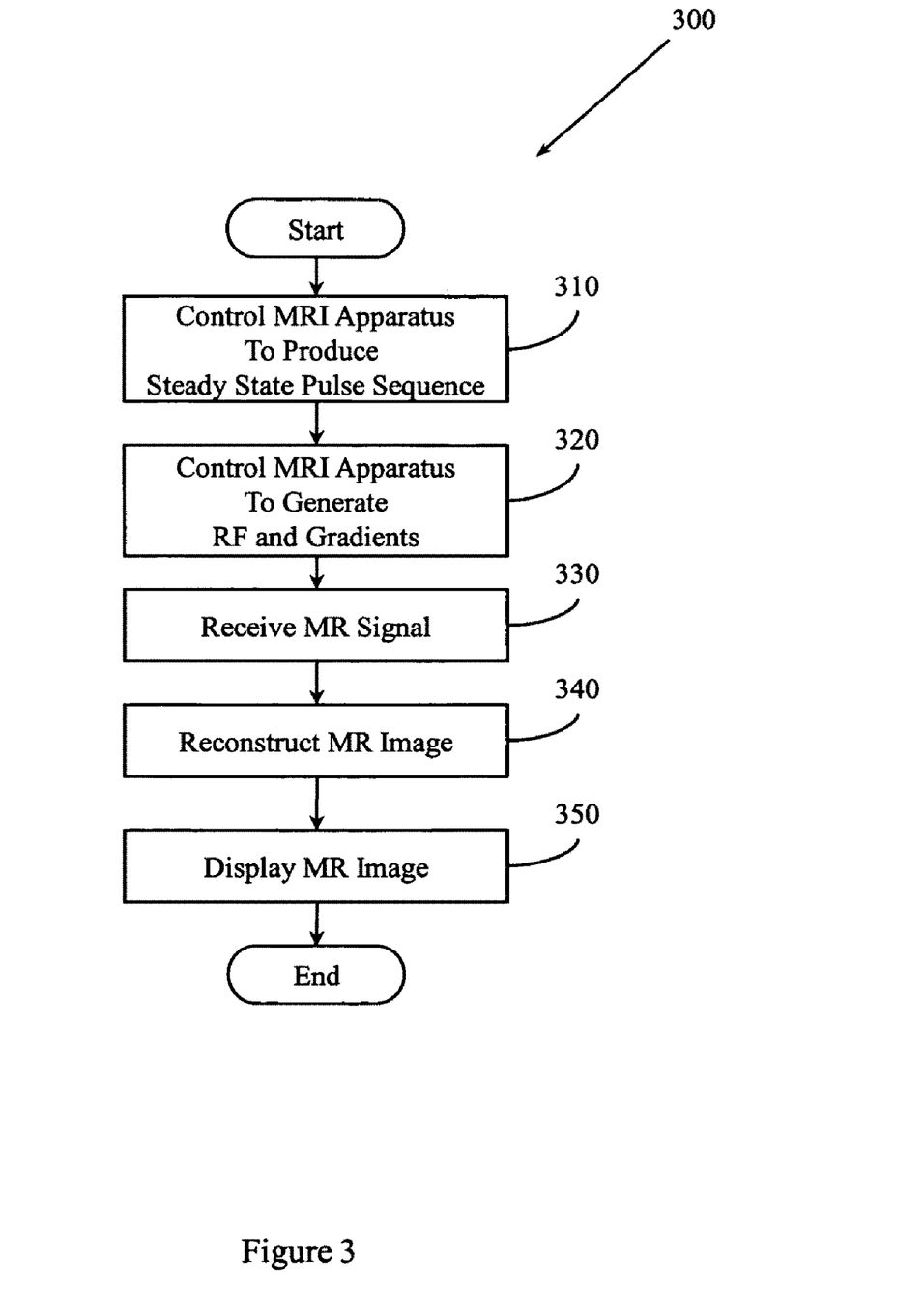
FIG. 3 illustrates an example method associated with steady state dark blood MRI.

FIG. 3 illustrates a method 300 associated with steady state dark blood MRI. Method 300 includes several actions similar to those described in connection with method 200 (FIG. 2). For example, method 300 includes controlling an MRI apparatus to produce a steady state pulse sequence at 310, and controlling an MRI apparatus to generate RF and gradients at 320. However, method 300 may include additional actions.

Method 300 may include, at 330, controlling the MRI apparatus to receive an MR signal from an object to be imaged in response to being exposed to the steady state pulse sequence. Note that signal is not received during the magnetization preparation modules as evidenced in FIG. 1 by the absence of the analog to digital controller being active during the illustrated saturation module. Thus, the MRI apparatus may be controlled to receive the MR signal during readout modules but not during magnetization preparation (e.g., saturation) modules.

Method 300 may also include, at 340, controlling the MRI apparatus to reconstruct an MR image from MR signal from a readout module. One skilled in the art will appreciate that various reconstruction approaches may be employed to reconstruct an image.

Method 300 may also include, at 350, controlling the MRI apparatus to display the MR image on a display. Thus, a concrete, tangible, real-world result is produced by the output of the reconstructed MR image on the display.

Figure 4:
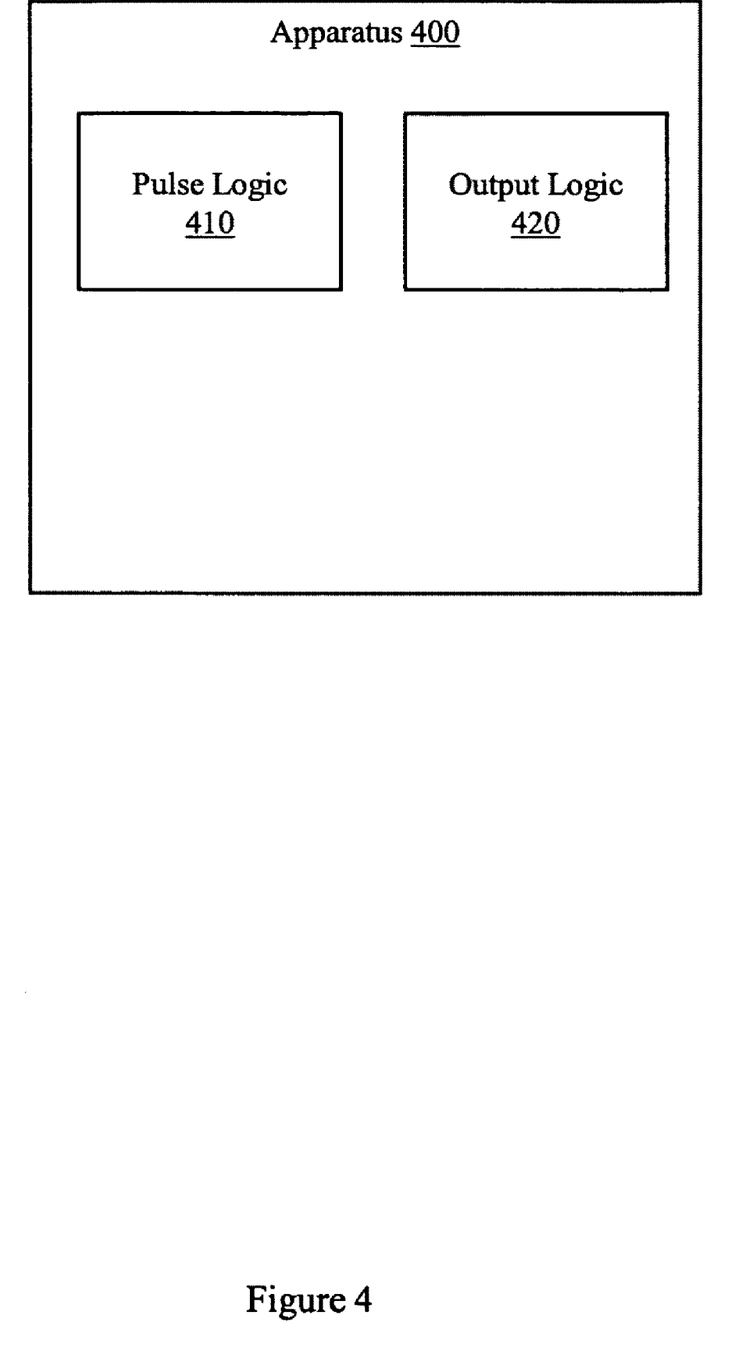
FIG. 4 illustrates an example apparatus associated with steady state dark blood MRI.

FIG. 4 illustrates an apparatus 400 associated with steady state dark blood MRI. Apparatus 400 includes a pulse logic 410 and an output logic 420. Pulse logic 410 is to produce a steady state pulse sequence that includes a set of readout modules and a set of magnetization preparation modules. Output logic 420 is to produce radio frequency (RF) energy and magnetic gradients associated with the steady state pulse sequence.

The steady state pulse sequence produced by pulse logic 410 is different from conventional steady sate pulse sequences. For example, the steady state pulse sequence includes regularly spaced in time slice selection excitation pulses to excite a region to be imaged in an object to be imaged using a consistent repetition time (TR), a readout module, and a magnetization preparation module. The magnetization preparation module facilitates preparing spins that may have previously contributed unwanted signal to an image to not provide that signal during a readout module in the steady state pulse sequence. This type of magnetization preparation may be achieved by having pulse logic 410 produce a steady state pulse sequence that controls output logic 420 during a magnetization preparation module to deactivate a gradient associated with magnetic resonance (MR) imaging, to activate RF pulses associated with slice selection, and to activate gradients associated with slice selection and dephasing.

Pulse logic 410 can produce a steady state pulse sequence that has different types of magnetization preparation modules. These magnetization preparation modules may include a saturation module, an inversion module, and a tagging module. A saturation module may be produced by having output logic 420 control a gradient associated with region selection and control RF pulses associated with region selection to excite a set of saturation regions located outside the region to be imaged. These are regions in which spins associated with blood flowing into the region to be imaged may be located.

Figure 5:
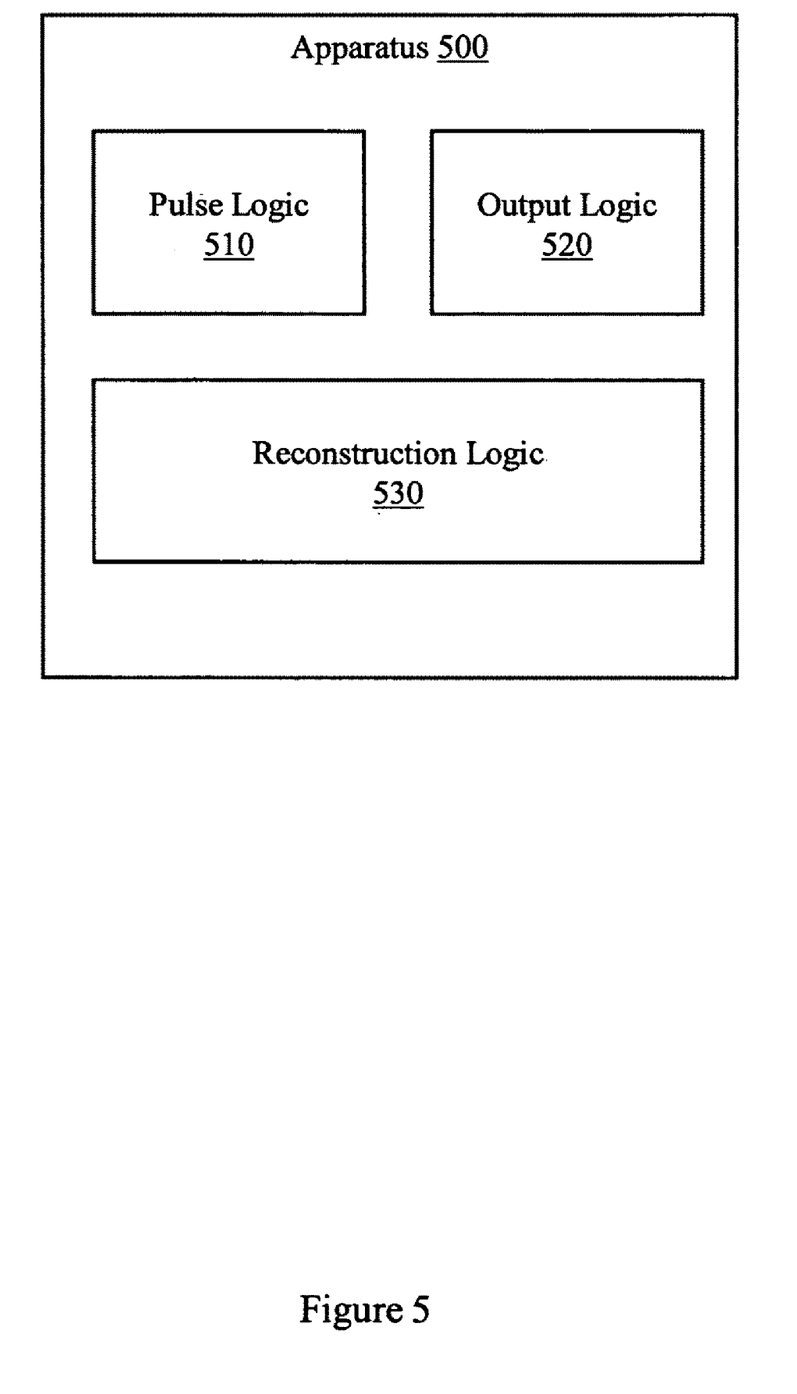
FIG. 5 illustrates an example apparatus associated with steady state dark blood MRI.

FIG. 5 illustrates an apparatus 500 associated with steady state dark blood MRI. Apparatus 500 includes items similar to those described in connection with apparatus 400 (FIG. 4). For example, apparatus 500 includes a pulse logic 510 and an output logic 520. However, apparatus 500 may include additional elements. For example, apparatus 500 includes a reconstruction logic 530. Reconstruction logic 530 is to reconstruct an MR image from signals received from the object to be imaged in response to the steady state pulse sequence. For example, reconstruction logic 530 may reconstruct an image of a blood vessel wall based on signals received from the blood vessel wall. The image may be superior to conventional images because signal from blood flowing in the blood vessel may be reduced due to saturation of regions (e.g., slabs, slices) outside the region to be imaged. The blood near the blood vessel wall at the time of imaging may have been located in the regions outside the region to be imaged when saturated and thus may contribute no signal in the region to be imaged at a later point in time.

Figure 6:
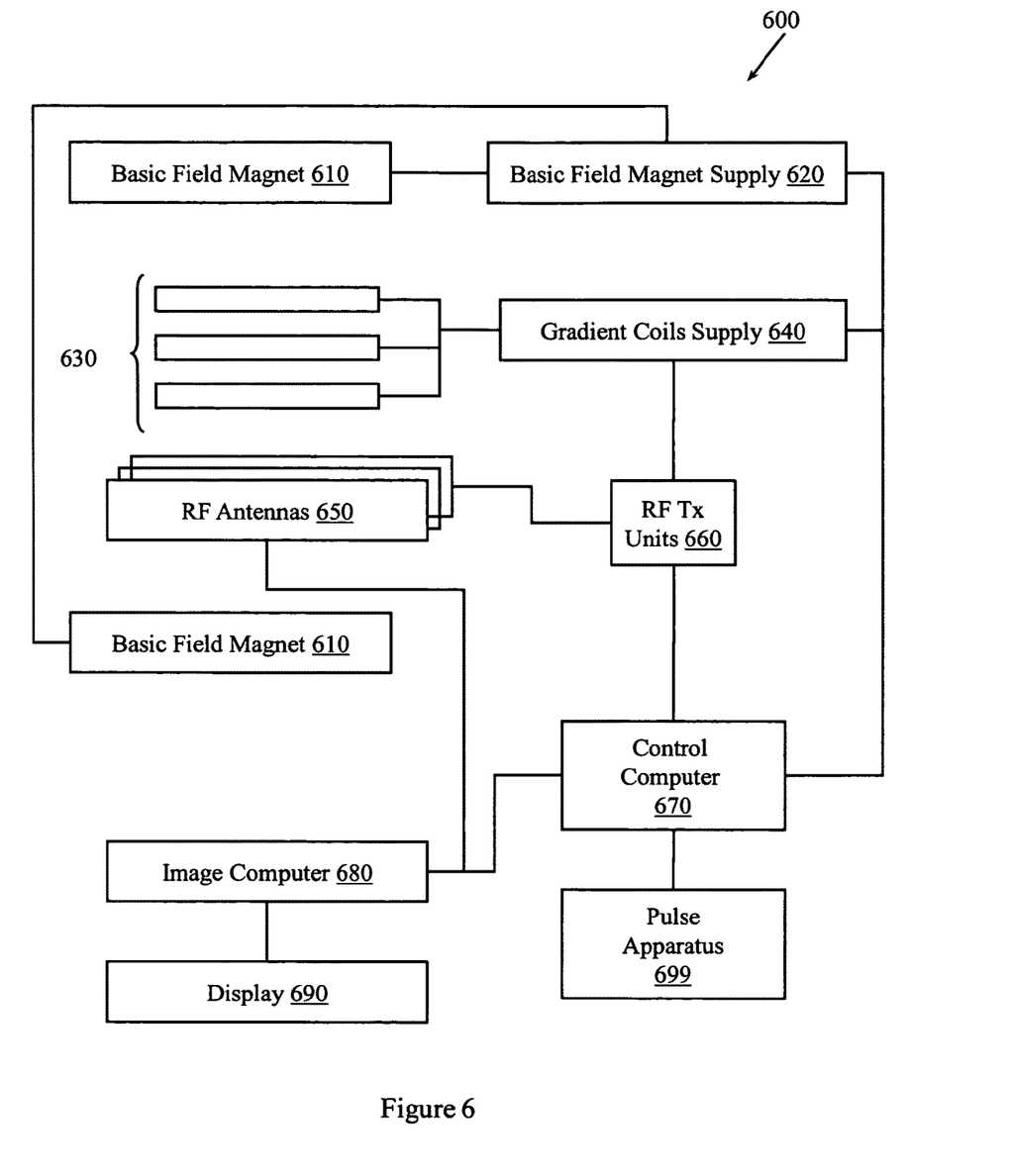
FIG. 6 illustrates an example system associated with steady state dark blood MRI.

FIG. 6 illustrates an example MRI apparatus 600 configured with a pulse apparatus 699 to facilitate dark blood imaging. The pulse apparatus 699 may be configured with elements of example apparatus described herein and/or may perform example methods described herein.

The apparatus 600 includes a basic field magnet(s) 610 and a basic field magnet supply 620. Ideally, the basic field magnets 610 would produce a uniform $B_0$ field. However, in practice, the $B_0$ field may not be uniform, and may vary over an object being imaged by the MRI apparatus 600. MRI apparatus 600 may include gradient coils 630 configured to emit gradient magnetic fields like $G_S$, $G_P$ and $G_R$. The gradient coils 630 may be controlled, at least in part, by a gradient coils supply 640. In some examples, the timing, strength, and orientation of the gradient magnetic fields may be controlled, and thus selectively adapted during an MRI procedure.

MRI apparatus 600 may include a set of RF antennas 650 that are configured to generate RF pulses and to receive resulting magnetic resonance signals from an object to which the RF pulses are directed. In some examples, how the pulses are generated and how the resulting MR signals are received may be controlled and thus may be selectively adapted during an MRI procedure. Separate RF transmission and reception coils can be employed. The RF antennas 650 may be controlled, at least in part, by a set of RF transmission units 660. An RF transmission unit 660 may provide a signal to an RF antenna 650.

The gradient coils supply 640 and the RF transmission units 660 may be controlled, at least in part, by a control computer 670. In one example, the control computer 670 may be programmed to control an MRI device as described herein. The magnetic resonance signals received from the RF antennas 650 can be employed to generate an image and thus may be subject to a transformation process like a two dimensional fast Fourier transform (FFT) that generates pixilated image data. The transformation can be performed by an image computer 680 or other similar processing device. The image data may then be shown on a display 690. While FIG. 6 illustrates an example MRI apparatus 600 that includes various components connected in various ways, it is to be appreciated that other MRI apparatus may include other components connected in other ways.

Figure 7:
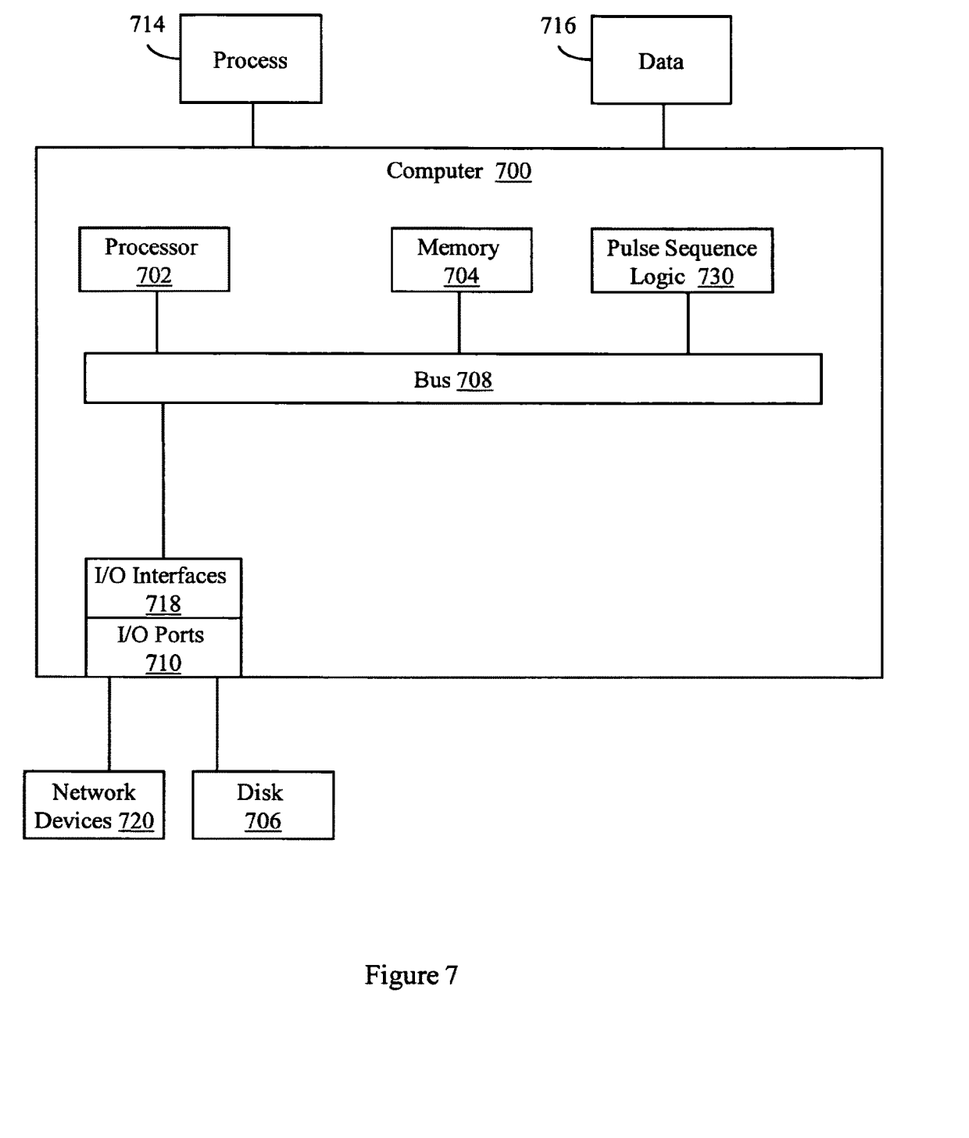
FIG. 7 illustrates an example computing environment in which example systems and methods, and equivalents, may operate.

FIG. 7 illustrates an example computing device in which example systems and methods described herein, and equivalents, may operate. The example computing device may be a computer 700 that includes a processor 702, a memory 704, and input/output ports 710 operably connected by a bus 708. In one example, the computer 700 may include a pulse sequence logic 730 configured to facilitate producing a modified steady state sequence which in turn facilitates superior dark blood MRI. In different examples, the logic 730 may be implemented in hardware, software, firmware, and/or combinations thereof. While the logic 730 is illustrated as a hardware component attached to the bus 708, it is to be appreciated that in one example, the logic 730 could be implemented in the processor 702.

Thus, logic 730 may provide means (e.g., hardware, software, firmware) for generating a steady state pulse sequence. The steady state pulse sequence may have regularly spaced slice selection excitation pulses to excite a region to be imaged in an object to be imaged using a consistent repetition time (TR). The steady state pulse sequence may also have a readout module and a magnetization preparation module. During a magnetization preparation module a gradient associated with MR imaging is not active, a gradient associated with slice selection is active, and RF pulses associated with slice selection are active. Signal from which an MR image can be reconstructed is to be acquired from the object to -be imaged during a readout module. Logic 730 may also provide means (e.g., hardware, software, firmware) for applying the steady state pulse sequence to an object to be imaged. Logic 730 may also provide means (e.g., hardware, software, firmware) for reconstructing a magnetic resonance image from signals acquired from the object to be imaged in response to applying the steady state pulse sequence. The means associated with logic 730 may be implemented, for example, as an ASIC programmed to control an MRI apparatus. The means may also be implemented as computer executable instructions that are presented to computer 700 as data 716 that are temporarily stored in memory 704 and then executed by processor 702 to control an MRI apparatus.

Generally describing an example configuration of the computer 700, the processor 702 may be a variety of various processors including dual microprocessor and other multi-processor architectures. A memory 704 may include volatile memory and/or non-volatile memory. Non-volatile memory may include, for example, ROM, PROM, and so on. Volatile memory may include, for example, RAM, SRAM, DRAM, and so on.

A disk 706 may be operably connected to the computer 700 via, for example, an input/output interface (e.g., card, device) 718 and an input/output port 710. The disk 706 may be, for example, a magnetic disk drive, a solid state disk drive, a floppy disk drive, a tape drive, a Zip drive, a flash memory card, a memory stick, and so on. Furthermore, the disk 706 may be a CD-ROM drive, a CD-R drive, a CD-RW drive, a DVD ROM drive, a Blu-Ray drive, an HD-DVD drive, and so on. The memory 704 can store a process 714 and/or a data 716, for example. The disk 706 and/or the memory 704 can store an operating system that controls and allocates resources of the computer 700.

The bus 708 may be a single internal bus interconnect architecture and/or other bus or mesh architectures. While a single bus is illustrated, it is to be appreciated that the computer 700 may communicate with various devices, logics, and peripherals using other busses (e.g., PCIE, 1394, USB, Ethernet). The bus 708 can be types including, for example, a memory bus, a memory controller, a peripheral bus, an external bus, a crossbar switch, and/or a local bus.

The computer 700 may interact with input/output devices via the i/o interfaces 718 and the input/output ports 710. Input/output devices may be, for example, a keyboard, a microphone, a pointing and selection device, cameras, video cards, displays, the disk 706, the network devices 720, and so on. The input/output ports 710 may include, for example, serial ports, parallel ports, and USB ports.

The computer 700 can operate in a network environment and thus may be connected to the network devices 720 via the i/o interfaces 718, and/or the i/o ports 710. Through the network devices 720, the computer 700 may interact with a network. Through the network, the computer 700 may be logically connected to remote computers. Networks with which the computer 700 may interact include, but are not limited to, a LAN, a WAN, and other networks.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, MB, MBB, MBBC, AABBCC, and so on (e.g., the data store may store only A, only B, only C, A&B, A&C, B&C, A&B&C, A&A&A, A&A&B, A&A&B&B, A&A&B&B&C, A&A&B&B&C&C, and so on). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A non-transitory computer-readable medium storing computer-executable instructions that when executed by a computer cause the computer to perform a method, the method comprising:
controlling a magnetic resonance imaging (MRI) apparatus to produce a steady state pulse sequence; and
controlling the MRI apparatus to generate radio frequency (RF) energy and magnetic gradients associated with the steady state pulse sequence;
where the steady state pulse sequence is characterized by:
regularly spaced in time slice selection excitation pulses to excite a region to be imaged in an object to be imaged using a consistent repetition time (TR),
a readout module comprising a gradient that is active between readout RF pulses but not during the readout RF pulses, and
a magnetization preparation module,
where during a magnetization preparation module
an additional RF pulse associated with slice selection is produced between RF pulses associated with producing steady state,
an additional fixed slice selection gradient correlated to the additional RF pulse is active between RF pulses in the readout module,
a fixed phase selection gradient is active at a time not overlapping with the additional RF pulse or the additional fixed slice selection gradient, and
a fixed readout gradient is active at a time correlated to the fixed phase selection gradient,
and
where signals from which an MR image of the object to be imaged can be reconstructed are to be acquired during the readout module.

2. The non-transitory computer-readable medium of claim 1, where the magnetization preparation module is a saturation module during which the method includes controlling production of a gradient associated with slice selection and the additional RF pulse associated with slice selection to excite a set of saturation regions located outside the region to be imaged.

3. The non-transitory computer-readable medium of claim 2, where the set of saturation regions includes an even number of regions and where the steady state pulse sequence includes an even number of saturation modules.

4. The non-transitory computer-readable medium of claim 1, where the method includes controlling a frequency of the magnetization preparation modules to change during acquisition to vary the amount of saturation preparation in relation to a position being encoded in k-space in an adjacent readout module.

5. The non-transitory computer-readable medium of claim 1, where the steady state pulse sequence includes a repeating pattern comprising an even number of consecutive readout modules followed by an even number of magnetization preparation sequences.

6. The non-transitory computer-readable medium of claim 5, where the method includes controlling the pulse sequence to apply a relatively larger number of saturation modules when an adjacent readout module is encoding a contrast determining center of k-space and to apply a relatively smaller number of saturation modules when an adjacent readout module is encoding a resolution determining outer region of k-space.

7. The non-transitory computer-readable medium of claim 1, where the magnetization preparation module is an inversion module.

8. The non-transitory computer-readable medium of claim 1, where the magnetization preparation module is a tagging module.

9. The non-transitory computer-readable medium of claim 8, where the method includes controlling, during the tagging module, one or more of, an MR gradient, and RF pulses to produce two different excitations in two different sets of spins, where a first excitation is produced in spins associated with an item that is moving in an imaging region, and where a second excitation is produced in spins that are associated with an item that is substantially static in the imaging region.

10. The non-transitory computer-readable medium of claim 1, where the steady state pulse sequence is one of, a true, fast imaging with steady state precession (TrueFISP) sequence, a fast low angle shot (FLASH) sequence, a fast imaging steady state precession (FISP) sequence, and a gradient reversed form of FISP (PSIF) sequence.

11. The non-transitory computer-readable medium of claim 1, where the method includes controlling gradients, during a magnetization preparation module, to be anti-symmetric gradients.

12. The non-transitory computer-readable medium of claim 1, where the magnetization preparation module is configurable with respect to one or more of, a position of a region to be prepared during the magnetization preparation module relative to the region to be imaged, a gap between the region to be prepared during the magnetization preparation and the region to be imaged, and a thickness of a region to be prepared during the magnetization preparation module.

13. The non-transitory computer-readable medium of claim 1, where the method includes controlling the steady state pulse sequence with respect to a ratio of magnetization preparation modules to readout modules.

14. The non-transitory computer-readable medium of claim 1, the method comprising:
controlling the MRI apparatus to receive a magnetic resonance (MR) signal from an object to be imaged in response to being exposed to the steady state pulse sequence.

15. The non-transitory computer-readable medium of claim 14, the method comprising:
controlling the MRI apparatus to reconstruct an MR image from the MR signal and to display the MR image on a display.

16. An apparatus, comprising:
a memory;
a processor; and
an interface that connects the processor, the memory, and a set of logics, the set of logics comprising:
a pulse logic to produce a steady state pulse sequence that includes a set of readout modules and a set of magnetization preparation modules; and an output logic to produce radio frequency (RF) energy and magnetic gradients associated with the steady state pulse sequence;

where the steady state pulse sequence includes:

regularly spaced in time slice selection excitation pulses to excite a region to be imaged in an object to be imaged using a consistent repetition time (TR), a readout module comprising a gradient that is active between readout RF pulses but not during the readout RF pulses, and a magnetization preparation module, where during a magnetization preparation module an additional RF pulse associated with slice selection is produced between RF pulses associated with producing steady state, an additional fixed slice selection gradient correlated to the additional RF pulse is active between RF pulses in the readout module, a fixed phase selection gradient is active at a time not overlapping with the additional RF pulse or the additional fixed slice selection gradient, and a fixed readout gradient is active at a time correlated to the fixed phase selection gradient, and where signal from which an MR image can be reconstructed is to be acquired from the object to be imaged during the readout module.

17. The apparatus of claim 16, comprising:

a reconstruction logic to reconstruct an MR image from signals received from the object to be imaged in response to the steady state pulse sequence.

18. The apparatus of claim 16, the magnetization preparation module being one or more of, a saturation module, an inversion module, and a tagging module.

19. The apparatus of claim 16, the magnetization preparation module being a saturation module during which a gradient associated with region selection and the additional RF pulse associated with region selection are configured to excite a set of saturation regions different from the region to be imaged.

20. A system, comprising:

means for generating a steady state pulse sequence having:

regularly spaced slice selection excitation pulses to excite a region to be imaged in an object to be imaged using a consistent repetition time (TR), a readout module comprising gradients between RF pulses but not including the RF pulses, and a magnetization preparation module, where during a magnetization preparation module:

an additional RF pulse associated with slice selection is produced between RF pulses associated with producing steady state, an additional fixed slice selection gradient correlated to the additional RF pulse is active between RF pulses in the readout module, a fixed phase selection gradient is active at a time not overlapping with the additional RF pulse or the additional fixed slice selection gradient, and a fixed readout gradient is active at a time correlated to the fixed phase selection gradient, and where signal from which an MR image can be reconstructed is to be acquired from the object to be imaged during [[a]] the readout module;

means for applying the steady state pulse sequence to an object to be imaged; and means for reconstructing a magnetic resonance image from signals acquired from the object to be imaged in response to applying the steady state pulse sequence.

* * * * *